United States Patent [19]

Millichip

[11] Patent Number: 4,885,241
[45] Date of Patent: Dec. 5, 1989

[54] ETHANOL PRODUCTION BY ZYMOMONAS CULTURED IN YEAST-CONDITIONED MEDIA

[75] Inventor: Robyn J. Millichip, Lincoln, Nebr.

[73] Assignee: University of Queensland, Queensland, Australia

[21] Appl. No.: 257,073

[22] Filed: Oct. 13, 1988

[51] Int. Cl.4 .................. C12R 1/38; C12P 39/00; C12P 7/06; C12P 7/14

[52] U.S. Cl. ...................... 435/42; 435/161; 435/162; 435/813; 435/822

[58] Field of Search ............. 435/42, 162, 161, 813, 435/822

[56] References Cited

U.S. PATENT DOCUMENTS

| | | | |
|---|---|---|---|
| 2,372,854 | 4/1945 | Reich | 435/162 |
| 3,093,548 | 6/1963 | Coates et al. | 435/162 |
| 4,350,765 | 9/1982 | Chibata et al. | 435/162 |
| 4,393,136 | 7/1983 | Cheetham | 435/161 |
| 4,403,034 | 9/1983 | Rogers et al. | 435/161 |
| 4,460,687 | 7/1984 | Ehnstrum | 435/162 |
| 4,731,329 | 3/1988 | Lawford | 435/162 |
| 4,797,360 | 1/1989 | Doelle | 435/161 |
| 4,808,526 | 2/1989 | Lawford | 435/161 |

FOREIGN PATENT DOCUMENTS

8800616  1/1988  World Int. Prop. O. .......... 435/162

OTHER PUBLICATIONS

Derwent Abs. 83-760898/37, Hitachi Zosen Corp, J58/29984 (8-83).

*Primary Examiner*—Herbert J. Lilling
*Attorney, Agent, or Firm*—Kilpatrick & Cody

[57] ABSTRACT

A process for producing ethanol in the substantial absence of fusel oils by Zymomonas fermentation wherein fermentation is carried out under conditions unfavorable for the growth and replication of yeast. In the preferred embodiment, Zymomonas are initially inoculated into a carbohydrate containing medium undergoing active fermentation by yeast, then the fermentation conditions altered to inhibit growth and replication of yeast.

6 Claims, No Drawings

ETHANOL PRODUCTION BY ZYMOMONAS CULTURED IN YEAST-CONDITIONED MEDIA

BACKGROUND OF THE INVENTION

The present invention relates to a process for fermenting carbohydrates using bacteria of the genus Zymomonas initially inoculated into yeast-conditioned media.

Ethanol production has traditionally been carried out in a two-stage, batch process employing yeast. The first stage of this process, in which the yeast are grown under aerobic conditions, is referred to as the "growth stage". The second stage entails the production, by fermentation, of ethanol under anaerobic conditions, i.e., in the presence of only small amounts, if any, of oxygen. Addition of air or oxygen is required if the yeast is to be propagated during the ethanol-producing second stage. In particular, oxygen is required if the efficiency of the total process is to be increased by the occasional recycling of yeast cells, for example, via sedimentation or centrifugation.

One disadvantage of the traditional process of yeast fermentation is its long fermentation time. "Fermentation time" is the period of time required for complete conversion of substrate to end products, or for the biocatalyst (the ethanol producing organisms) to reach the stage of maximum yield of end-products. At a preferred optimal temperature of between 30° and 40° C., 30- to 70-hour fermentation times have been necessary to obtain 9% to 11% (v/v) ethanol when yeast cells are used for conversion of glucose to ethanol. The rate-limiting factors in this process are the rates of glucose uptake and ethanol production by individual yeast cells. These rates are stringently regulated by cellular enzyme control systems.

One method devised to increase the yield of ethanol is to use a larger inoculum of yeast cells, i.e., a larger biomass density. However, even when using a cell density of 5–10 million cells per milliliter (mL), this method still requires 30–50 hours of fermentation time. Reduction in fermentation time to the range of 10–30 hours has been achieved by using 30–100 times higher biomass density in a two-stage batch process. This higher biomass density is achieved by recycling cells previously used in another fermentation. However, the higher biomass density requires an adequate supply of nutrients, supplies of which are often limited.

Another disadvantage of the yeast fermentation process, especially when cost is a major concern, is the diversion of fermentable substrate to the production of by-products such as glycerol, amylalcohol and other fusel oils. As a result, the efficiency of conversion of substrate to end-product, e.g., from glucose to ethanol, is lower than desirable, i.e., only between 85 and 91%.

Efforts to increase the yield of ethanol from sugar fermentation has also been limited by the sensitivity of yeast cells to high concentrations of both the sugar substrate ("substrate inhibition") and the ethanol end-product ("end-product inhibition"). Substrate inhibition results from an osmotic effect of the substrate on the cells, and is reflected in reduced water activity inside the cell, plasmolysis, and decreased viability. End-product inhibition results from high solubility of cell membranes in ethanol and feedback inhibition. In either case, there is inhibition of cell growth or fermentation.

To overcome the drawbacks of yeast-based fermentation, attempts have been made to use Zymomonas bacteria instead of yeast. Zymomonads, such as *Z. mobilis*, are a very limited class of facultative anaerobic bacteria that metabolize glucose via the Entner-Doudoroff pathway, usually found in strictly aerobic microorganisms. Strains of *Z. mobilis* have been shown to have rates of glucose uptake and ethanol production, respectively, that are several times higher than yeast, as well as higher ethanol-yield values, reflecting the ability of the strains to tolerate high concentrations of both sugar and ethanol.

Notwithstanding the potential advantages of Zymomonas bacteria compared to yeast, the development of practical fermentation systems employing the bacteria has lagged, at least in part due to a serious contamination problem associated with the use of Zymomonas in high-sugar fermentation environments. Gram-negative Zymomonas cells growing under commercial plant conditions are often overwhelmed by competition from contaminating microflora, principally gram-positive bacteria, before the fermentative bacteria can become established, effectively precluding the increase in zymomonad biomass that is necessary to accomplish industrial-scale fermentation, typically requiring volumes greater than 1000 gallons.

In the face of problems with both yeast-based and zymomonad-based fermentations, it has been proposed to use mixed cultures of yeast and Zymomonas cells under conditions that would permit both types of fermentative microorganisms to function in the same environment. Generally, a mixed-culture is prepared from yeast and bacteria which have initially been cultured separately until they reach a logarithmic growth phase, that are then mixed together in similar proportions. The yeast/bacterial mixture is then added to a substrate, such as sucrose, fructose, or glucose, that is fermentable by both the yeast and Zymomonas.

The conditions present in a mixed culture must be applicable to the reproduction and fermentation of both organisms; i.e., both yeast and Zymomonas. A mixed culture requires that the populations of the two organisms reach an equilibrium, and remain stable throughout the fermentation process.

It is very difficult to maintain culture conditions which allow for reproduction of both organisms and maximum fermentation by both organisms. In order to maintain conditions for the propagation of one organism, the other will suffer. For example, air is needed for yeast to propagate, however, air interferes with the fermentation capabilities of the Zymomonas. Anaerobic conditions, on the other hand, will promote ethanol production by both the yeast and Zymomonas; however, the yeast will not propagate, their population will diminish, and a stable population will not be maintained. High ethanol concentrations will also inhibit yeast, whereas Zymomonas have been reported by Burrill et al., *Biotech Letters* 5(6), 423–428 (1983), to tolerate up to 150 ml ethanol/l before being inhibited. Further, Zymomonas are also unable to utilize urea, a nutrient that is the most commonly accepted nutrient for ethanol production by yeasts in the ethanol industry today.

Mixed cultures are not suitable in many of the fermentation methods already in use in the ethanol industry. For example, mixed cultures of yeast and zymonads cannot be grown using continuous fermentation, such as the Vogelbusch technology, which is based on the maintenance of a steady state population of a particular organism by using the dilution rate of the media to maintain and equal the growth rate of the organism. Every organism has its own growth rate at any particular dilution rate which determines which organism will predominate. If a contaminant organism has a higher growth rate than the yeast, it will become the dominant organism; on the other hand, if the yeast has the higher growth rate, the yeast will predominate.

Other conditions, such as pH, temperature, antibiotics, and nutritional supplements, can also alter the growth rate of an organism, giving the opportunity for a new organism to take over. Under conditions such as these, it is virtually impossible for two organisms to remain co-dominant, as required for the successful functioning of a mixed culture.

Even where the two organisms in a mixed culture can be grown together successfully, the disadvantage remains with respect to production of ethanol by the yeast, i.e., the yeast will still produce fusel oils and the yield of ethanol from substrate will remain unchanged.

It is therefore an object of the present invention to provide a fermentation process that exploits the beneficial properties of Zymomonas while avoiding problems with contamination by other bacteria.

It is another object of the present invention to provide a fermentation system that can accommodate high-sugar feedstocks, affording high ethanol-yield values, without the necessity of maintaining mixed yeast-Zymomonas cultures.

It is still another object of the present invention to improve the efficiency of ethanol fermentation by eliminating simultaneous fusel oil production.

It is a further object of the present invention to minimize the time required for ethanol fermentation by Zymomonas.

SUMMARY OF THE INVENTION

A method for producing ethanol from fermentation of a substrate by Zymomonas wherein the Zymomonas are added to the fermentation medium after it has first been conditioned by a fermenting yeast culture.

In the preferred embodiment, Zymomonas inoculum in growth phase is added to a fermenting carbohydrate containing medium in which yeast have been cultured for the previous 24 hours. No additional yeast, urea, yeast nutrients, or air is added to the culture medium after addition of the zymomonads. Under these conditions, the yeast will eventually decline in population as the Zymomonas increase in number.

Zymomonas cultured in this manner produce high yields of ethanol with very little, if any, fusel oil contamination.

DETAILED DESCRIPTION OF THE INVENTION

A process for converting a fermentable carbohydrate to ethanol having the following steps:

(A) providing, in a first volume, a yeast culture in fermenting phase in a carbohydrate containing medium;

(B) adding a second volume of liquid containing Zymomonas culture that is in a growth phase to the yeast containing first volume to form a third volume; and thereafter (C) culturing the third volume under conditions which do not promote growth and proliferation of yeast.

The present invention overcomes the problem of the virtual destruction of Zymomonas cultures by microbial infection, a problem which has to date restrained the use of Zymomonas in commercial fermentation operations. In particular, it has been found that a Zymomonas culture, upon introduction into a new fermentation environment, must go through an "acclimatization" period before it is able to compete effectively with microflora indigenous to that environment. For reasons not fully understood, the addition of a growth-phase culture of Zymomonas bacteria to yeast-conditioned medium helps to ensure survival of the Zymomonas during the acclimatization period. Several factors are believed to be important, including the heat generated by the fermenting yeast in the initial hours following inoculation with the Zymomonas and products generated by the yeast which are beneficial to the Zymomonas but detrimental to other organisms.

"Culture" is used herein to denote an inoculated nutritive medium that contains living cells, whether yeast or bacterial. For present purposes, the makeup of a medium used with a given microorganism (yeast or bacterial) is not critical, so long as the medium contains at least the minimum components: a carbon source, a nitrogen source, vitamins, trace elements, etc., needed to sustain that microorganism. The minimum requirements for both yeast and Zymomonas media are known to those skilled in the art, for example, as described by Rogers, et al., *Adv. Biochem. Eng'g & Biotechnol.* 23: 37, 40-44 (1982), and generally contain some combination of yeast extract, peptone, diammonium phosphate, ammonium phosphate, magnesium sulfate, potassium dihydrogen phosphate, and urea. An example of a defined culture media is 5-10% glucose, 0.2-0.3% yeast extract, casein hydrolysate, 0.2% $MgSO_4.7H_2O$, $KH_2PO_4$, and $(NH_3)_2SO_4$.

Any Zymomonas that is capable of converting a fermentable carbohydrate to ethanol can be used in the present invention. An example of a useful strain is available from the American Type Culture Collection, Rockville, MD as strain ATCC 39767. Useful bacteria include those currently classified taxonomically as *Z. mobilis* and *Z. anaerobia*, although there is considerable uncertainty over the taxonomical classification of Zymomonas species.

A number of yeast strains known to those skilled in the art may be used. Such strains are available from the ATCC and other commercial sources. Suitable yeasts include those of the genera Saccharomvces and Kluyveromyces, *Pachysolen tannopholus*, and *Candida lusitaniae*.

A yeast-conditioned medium used pursuant to the present invention will typically have sustained yeast-based fermentation for at least twelve hours. Accordingly, a suitable medium can be expected to contain ethanol, usually in a concentration of greater than 1% (v/v). The pH should preferably be greater than 4 to promote growth of Zymomonas. pH adjustments are preferably made with $NH_3$.

The process of the present invention can be conducted via a "cascade" of fermentation reactors or in a batch process. Such methods are known to those skilled in the art.

The production of a Zymomonas culture that is in a growth phase, i.e., a culture wherein the bacterial cells are actively dividing, can be established by suspending the contents of an ampoule of Zymomonas bacteria in a small volume, for example, about 100 ml, of semi-defined medium. When the bacteria begin to reproduce, the 100 ml-sample is inoculated into a larger volume, for example, approximately 600 ml of semi-defined medium, and so forth, until a culture consisting of several liters is obtained.

To the latter, liter-scale volume is added a carbohydrate material which is fermentable by zymomonas, e.g., a material containing glucose, fructose, or, for some strains, sucrose. Suitable feedstocks in this regard include sucrose-based compositions like sugar cane juice and syrup, sugar beet juice and syrup, raw and refined sugar, palm sugar juice and syrup, and molasses; and glucose-fructose mixtures such as high fructose corn syrup, high test molasses (molasses treated with invertase to convert some sucrose therein to glucose and fructose), and other sugar solutions. Other fermentable materials include starch hydrolysates, which are complex mixtures obtained by treating liquefied starch with amyloglucosidase and which contain, as major components, glucose, maltrin, dextrin, maltose, lipids and proteins. Starch hydrolysates can be produced from liquified starch, a mixture of mltrin, dextrin, starch, lipids and proteins obtained from wet or dry milling of starch-containing plant and root materials, the product of which is treated with physical agents (high temperature and pressure), chemical agents (to effect acid hydrolysis) or α-amyloglucosidase, to lower viscosity and allow the use of a higher concentration in the fermentable mixture. The amyloglucosidase is generally used at a concentration of between 0.01 and 1.0%, preferably at a concentration of between 0.1 and 0.5%. Preferred materials include milo and corn.

At intervals ranging from about six to twelve hours each, the volume containing the growth-phase Zymomonas culture and fermentable carbohydrate is increased to the desired industrial-scale volume, preferably via successive additions of feedstock prepared as described above. When the zymomonas-containing medium thus produced is on the order of a hundred gallons, it is mixed with yeast-conditioned medium to which no penicillin, tetraformate or other anti-Zymomonas bacterial agent has been added, to a level of approximately 10 to 20% (v/v) of the total.

This mixture is not actively aerated, i.e., no oxygen or other gases are added to the fermentation vat, nor are any yeast nutrients added, although a phosphate supplement, such as diammonium phosphate, which is usable by the bacteria can be added. The fermentation medium is assayed periodically for ethanol content in order to track the evolution of bacteria-mediated fermentation.

When the rate of ethanol production is indicative of fermentation by the Zymomonas, i.e., higher than that typically seen with yeast, then further additions of fermentable material can be made to bring the final volumes to industrial levels, generally in the range of at least 8,500 gallons. At such volumes, periodic agitation is usually needed to keep the microbial cells suspended in the medium and to dissipate fermentation-generated heat. Using this methodology, conversion efficiencies in the range of 92-97% can be achieved.

The method of the present invention is distinguished from methods using "mixed culture" fermentation since the Zymomonas are grown under conditions which are designed only to promote the growth of one type of organism, the Zymomonas, not two types of organisms. In the latter situation, conditions are such that both Zymomonas and yeast thrive and metabolize carbohydrates, and the relative numbers bacterial and yeast cells, initially on the same order of magnitude, remain stable. A typical yeast fermentation would be expected to produce bacterial and yeast counts of 150 million viable cells per milliliter. In Examples 3 and 4, demonstrating the present invention, there were almost no viable yeast cells after several cascades, indicating that the yeast cells were not contributing to the fermentation of the substrate. As fermentation progresses without reproduction or replacement of the yeast, the relative number of yeast cells declines.

The decline in number of yeast is due in part to the process being conducted such that little or no air is introduced into the system once the Zymomonas are added to the yeast containing medium. Yeast do not grow under anaerobic conditions. By the same token, the process of the present invention preferably excludes any step of adding urea or other nitrogenous nutrient used solely by yeast to the Zymomonas cells. It is also preferred that the Zymomonas mediated fermentation proceed at a temperature above 35° C., up to about 41° C., in excess of the temperature at which yeast are normally cultured.

The present invention is further described by reference to the following non-limiting examples.

EXAMPLE 1

Normal Production of Ethanol by Yeast Fermentation

Cascade fermentation is conducted in a series of large fermentation vats. For example, starting with a completely empty fermenter, 44 lbs dried yeast is added to 8,400 gallons of milo mash. An additional 8,400 gallons of milo mash is subsequently added to the yeast containing mash to bring the total volume to 16,800 gallons. Approximately 4-6 hrs after the yeast is added to the first batch, 1,000 gallons along with an additional 22 lbs dry yeast, 15 lbs urea, 15 lbs yeast food, 2.25 lbs Alcoholase II powder and two liters tetraformate, is gravity-fed to a second fermenter. This is agitated and aerated for approximately 4 hrs. 0.25 lbs of penicillin is then added and the volume brought up to 8,400 gallons with milo mash. 1,000 gallons is then gravity-fed to the next fermenter, and the remaining 7,400 gallons is brought up to 16,800 gallons with milo mash. The process is repeated several times, resulting in a number of vats containing active yeast cultures.

Yeast fermentation is normally conducted at a pH between 3.5 and 4.5 and a temperature between 29 and 35 C. Maximum yeast reproduction occurs under aerobic conditions. Maximum ethanol production occurs under anaerobic conditions and in the presence of low levels of ethanol. Usually aeration is balanced to allow both growth and ethanol production. In a fermentation vat containing 150-200 million cells per ml of fermentable substrate, final levels of about 9-11% (v/v) ethanol can be achieved in 30 to 70 hours. The fermentation time is decreased by increasing the cell number. The heat produced by the fermentation is generally controlled by cooling coils.

When a fermentation was conducted using 15 lbs of yeast added to a final volume of 17,000 gallons milo mash was conducted, at the end of the fermentation (79 hrs), a level of 9.9% ethanol had been achieved. pH was 3.52. The product contained fusel oils.

EXAMPLE 2

Ethanol production using conventional fermentation by Zymomonas

There are also two stages involved in ethanol production by Zymomonas. In the first stage, conducted under anaerobic conditions, preferably at a pH between 4 and 8 and at a temperature between 20 and 40 C, most preferably at a pH of about 5.5 and a temperature of about 30 C, the bacteria are inoculated into a nutrient containing medium and allowed to replicate. In the second stage, additional carbon sources are added to the cells which, unlike yeast, are able to produce ethanol in the absence of growth.

As starting material for the studies described in the remaining examples, an ampoule of *Zymomonas mobilis* UQM 2716 (deposited with the University of Queensland Microbiology Department Culture Collection, St. Lucia, Queensland, Australia and the American Type Culture Collection, Rockville, Md. as deposit No. 39676) was suspended in 100 ml of semi-defined media: 5–10% glucose, 0.2–0.3% yeast extract, casein hydrolysate, 0.2% $MgSO_4$ $7H_2O$, $KH_2PO_4$, $(NH_3)_2SO_4$. Upon evidence of activity this was transferred into 600 ml semi-defined media, then into three liters of semi-defined media.

The three liters of growing bacteria was then added to five gallons of milo, then after approximately 12 hrs into 30 gallons, then 250 gallons of milo mash. Each of these steps represents approximately a 15% inoculum into the next stage.

The 250 gallons of Zymomonas inoculated mash was then introduced into 1,000 gallons of milo mash (or corn) with no additives other than an enzyme to cleave the saccharides in the milo, such as amigase, added at the same time as the milo, and between 0.10 g and 1.0 g DAP fertilizer/l, added once the fermenter was half full. Agitation was left on once the fermenters were full. pH was not controlled during the fermentation. Nisaplin, a commercial nisin concentrate produced by Aplin and Barrett, Ltd., was added beginning with the third cascade to control non-Zymomonas bacterial growth.

The fermenter was filled in two stages up to a 17,000 gallon level when approximately 3–5% (v/v) of ethanol was produced.

The conventional manner of producing ethanol by Zymomonas fermentation has been to inoculate the Zymomonas directly into a clean, disinfected fermenter. In one fermenter in which this procedure was followed, problems became apparent almost immediately. The Zymomonas culture became contaminated with both Gram positive bacteria, principally lactobacilli, and Gram negative bacteria. Despite the addition of glucose, amigase, and $NH_3$, the Zymomonas did not do well and the fermentation was discontinued after 11 hrs. The fermentation medium smelled bad and contained only 1.4% ethanol.

EXAMPLE 3

Production of ethanol using fermentation by Zymomonas inoculated into yeast-conditioned medium

*Zymomonas mobilis* was grown up as described to the 100-gallon stage. At this point, however, instead of adding this to 1,000 gallons of plain milo mash, it was added to 1,000 gallons of a 24-hr-old yeast fermentation, described in Example 1, to which neither penicillin or tetraformate had been added. No additional yeast, urea, yeast food, alcoholase II powder or air was added. 1.0 g DAP fertilizer/liter was added. The mixture was not agitated.

After approximately 6 hrs, the fermenter was filled in two stages to 17,100 gallons. Agitation was begun and 1.0 g DAP fertilizer/l was added. After approximately 6 hours the pH was 4.58 and the medium contained 3.9% ethanol. The fermenter was then filled in two stages to 17,100 gallons. Agitation was begun and 1.0 g DAP fertilizer/l was added. The Zymomonas were then cultured under conditions not promoting yeast growth or ethanol production. During the fermentation, additional amigase was added and the pH adjusted to above 4.0 with $NH_3$. The fermentation was continued for 57½ hrs.

Good yields of ethanol were obtained. Levels of 10.3% ethanol were achieved for a final yield of 2.67 gallons ethanol/bushel milo.

EXAMPLE 4

Ethanol production from cascade fermentation by Zymomonas 2500 gallons from the fermenter in Example 3 was used to cascade as a 15% inoculum into a second 18,000 gallon fermenter after 23 hours when the ethanol reading was 5.7%. A 15% inoculum from the second fermenter was used to inoculate a third fermenter, and so on to give a total of eight completed fermentations. The initial yeast count declined substantially with each cascade. The last three cascades were made using corn instead of milo as the fermentation substrate.

Excellent yield was obtained, with an average yield of just under 2.5 gallons ethanol/bushel of carbohydrate, with the highest yield from the last cascade, 2.7 gallons ethanol/bushel of corn. Levels of alcohol ranged from 9.2 to 10.5% (v/v). After the contents of the last six fermenters were distilled, no more than one quart of fusel oils was produced.

These examples demonstrate that maximum yield of ethanol from substrate is obtained by fermentation of Zymomonas under conditions not promoting growth and fermentation by yeast or other organisms, where the Zymomonas is initially combined with the substrate containing an actively growing yeast culture.

Modifications and variations of the present invention, a method for the production of ethanol by fermentation by Zymomonas of a carbohydrate material utilizing a starting fermentation medium conditioned by prior yeast fermentation, will be obvious to those skilled in the art from the foregoing detailed description of the invention. Such modifications and variations are intended to come within the scope of appended claims.

We claim:

1. A process for converting a fermentable carbohydrate to ethanol comprising:
   (a) providing a culture medium containing a fermentable carbohydrate and yeast in the fermenting phase containing carbohydrate substrate fermentable by Zymomonas, wherein said culture medium does not contain any anti-Zymomonas agents;
   (b) adding Zymomonas to said yeast containing culture medium; and
   (c) culturing the yeast-Zymomonas under anaerobic conditions at a pH of greater than about 4 to promote growth of the Zymomonas and not the yeast.

2. The process of claim 1 wherein the volume of the medium containing the Zymomonas is equal to or less than 20% (v/v) of the combined volume of the yeast and Zymomonas.

3. The process of claim 1 wherein the combined yeast-Zymomonas are cultured at temperatures between approximately 35° C. and 41° C.

4. The process of claim 1 wherein the combined yeast-Zymomonas are cultured without added yeast nutrients.

5. The process of claim 1 wherein the combined yeast-Zymomonas are cultured with greater than 1% (v/v) ethanol.

6. The process of claim 1 wherein the combined yeast-Zymomonas are cultured in a volume greater than 1,000 gallons.

* * * * *